US005830917A

United States Patent [19]
Moore et al.

[11] Patent Number: 5,830,917
[45] Date of Patent: Nov. 3, 1998

[54] L-N$^6$-(1-IMINOETHYL) LYSINE DERIVATIVES USEFUL AS NITRIC OXIDE SYNTHASE INHIBITORS

[75] Inventors: William M. Moore, St. Charles, Mo.; E. Ann Hallinan, Evanston, Ill.

[73] Assignee: G. D. Searle & Co., Skokie, Ill.

[21] Appl. No.: 526,147

[22] Filed: Sep. 11, 1995

[51] Int. Cl.$^6$ ................ A61K 31/18; A61K 31/155; C07C 279/12; C07C 311/05
[52] U.S. Cl. .............. 514/634; 514/601; 514/605; 514/631; 514/636; 514/637; 514/824; 514/866; 514/921; 514/929; 564/98; 564/99; 564/225; 564/236; 564/237; 564/240; 564/243
[58] Field of Search ..................... 564/225, 243, 564/236, 237, 240, 98, 99; 514/631, 634, 636, 637, 601, 605, 824, 866, 929, 921

[56] References Cited

U.S. PATENT DOCUMENTS

| | | | |
|---|---|---|---|
| 3,499,927 | 3/1970 | Badcock et al. | 564/236 |
| 4,713,369 | 12/1987 | Süber | 514/18 |
| 5,059,712 | 10/1991 | Griffith | 562/560 |
| 5,081,148 | 1/1992 | Braquet et al. | 514/162 |
| 5,132,453 | 7/1992 | Griffith | 562/560 |
| 5,196,450 | 3/1993 | Sjoerdsma et al. | 514/565 |
| 5,242,947 | 9/1993 | Cherksey et al. | 514/628 |
| 5,273,875 | 12/1993 | Griffith | 435/1 |
| 5,281,627 | 1/1994 | Griffith | 514/565 |
| 5,362,744 | 11/1994 | Purchase, Jr. et al. | 514/381 |
| 5,380,945 | 1/1995 | Murad et al. | 564/108 |

FOREIGN PATENT DOCUMENTS

| | | |
|---|---|---|
| 0370320 | 5/1990 | European Pat. Off. . |
| 0446699 | 9/1991 | European Pat. Off. . |
| 2240041 | 7/1991 | United Kingdom . |
| 91/04023 | 4/1991 | WIPO . |
| 91/04024 | 4/1991 | WIPO . |
| 93/13055 | 7/1993 | WIPO . |
| 93/16721 | 9/1993 | WIPO . |
| 93/24126 | 12/1993 | WIPO . |
| 94/14780 | 7/1994 | WIPO . |
| 95/00505 | 1/1995 | WIPO . |
| 95/11014 | 4/1995 | WIPO . |

OTHER PUBLICATIONS

Gould et al., "Nucleoside Intermediates in Blasticidin S Biosynthesis Identified by the In Vivo Use of Enzyme Inhibitors", *Can. J. Chem.*, vol. 72, pp. 6–11, 1994.

Tsunematsu et al., "β–Naphthylamides of Guanidinophenyl Amino Acids as Substrates of Aminopeptidases", *Chem. Pharm. Bull.*, vol. 36, No. 3, pp. 1205–1209, 1988.

Funabashi et al., "A New Atni–MRSA Dipeptide, TAN–1057 A", *Tetrahedron*, vol. 49, No. 1, pp. 13–28, 1993.

Prabhakaran et al., "Studies on Nitrogen Metabolism Using $^{13}$C NMR Spectroscopy. 5.$^1$ Metabolism of L–α–Arginine in the Biosynthesis of Blasticidin S", *Tetrahedron*, vol. 27, No. 33, pp. 3815–3818, 1986.

Stuehr et al., "Mammalian Nitric Oxide Syntheases", *Advances in Enzymology*, vol. 65, 1992, (p. 317).

Plapp et al., "Determination of ε–Acetimidyllysine in Proteins" *Analytical Biochemistry*, vol. 62, pp. 291–294, 1974.

Rees et al., "Characterization of Three Inhibitors of Endothelial Nitric Oxide Synthase in vitro and in vivo", *Br. J. Pharmacol.*, vol. 101, pp. 746–752, 1990.

Proudfoot et al., "Conformation–directed Recombination of Enzyme–activated Peptide Fragments: A Simple and Efficient Means to Protein Engineering", *J. Bio. Chem.*, vol. 264, No. 15, pp. 8764–8770, 1989.

Palacios, et al., "Nitric Oxide from L–Arginine Stimulates the Soluble Guanylate Cyclase in Adrenal Glands", *Biochemical and Biophysical Research Communications*, vol. 165, No. 2, pp. 802–809, 1989.

Knowles et al., "Kinetic Characteristics of Nitric Oxide Synthase from Rat Brain", *Biochem. J.*, vol. 269, pp. 207–210, 1990.

CA 107, 40336y, 1987.
CA 63, 5641d, 1995.
CA 97, 38442m, 1982.
CA 76, 43768t, 1972.
CA 118, 72838g, 1993.
CA 64, 17593h, 1966.
CA 115, 29868t, 1991.
CA 104, 202858, 1986.
CA 110, 228216, 1989.
CA 105, 225818, 1986.
Morimoto et al., ZA 8502512, cited in Chem. Abst., 105:225818, 1986.

*Primary Examiner*—Peter O'Sullivan
*Attorney, Agent, or Firm*—Banner & Witcoff, Ltd.; Dennis A. Bennett

[57] ABSTRACT

There is disclosed a novel amino alcohol amine derivatives of L-N$^6$-(1-iminoethyl)lysine, pharmaceutical compositions containing these novel compounds, and to their use in therapy, in particular their use as nitric oxide synthase inhibitors.

12 Claims, No Drawings

L-N⁶-(1-IMINOETHYL) LYSINE DERIVATIVES USEFUL AS NITRIC OXIDE SYNTHASE INHIBITORS

BACKGROUND OF THE INVENTION

1. Field of the Invention

The present invention relates to novel amino alcohol amine derivatives of L-N⁶-(1-iminoethyl)lysine, pharmaceutical compositions containing these novel compounds, and to their use in therapy, in particular their use as nitric oxide synthase inhibitors.

2. Related Art

It has been known since the early 1980's that the vascular relaxation brought about by acetycholine is dependent on the presence of the endothelium and this activity was ascribed to a labile humoral factor termed endothelium-derived relaxing factor (EDRF). The activity of nitric oxide (NO) as a vasodilator has been known for well over 100 years and NO is the active component of amylnitrite, glyceryltrinitrite and other nitrovasodilators. The recent identification of EDRF as NO has coincided with the discovery of a biochemical pathway by which NO is synthesized from the amino acid L-arginine by the enzyme NO synthase.

NO is the endogenous stimulator of the soluble guanylate cyclase and is involved in a number of biological actions in addition to endothelium-dependent relaxation including cytotoxicity of phagocytic cells and cell-to-cell communication in the central nervous system (see Moncada et al, *Biochemical Pharmacology*, 38, 1709–1715 (1989) and Moncada et al, *Pharmacological Reviews*, 43, 109–142 (1991). It is now thought that excess NO production may be involved in a number of conditions, particularly conditions which involve systemic hypotension such as toxic shock and therapy with certain cytokines.

The synthesis of NO from L-arginine can be inhibited by the L-arginine analogue, L-N-monomethyl-arginine (L-NMMA) and the therapeutic use of L-NMMA for the treatment of toxic shock and other types of systemic hypotension has been proposed (WO 91/04024 and GB-A-2240041). The therapeutic use of certain other NO synthase inhibitors apart from L-NMMA for the same purpose has also been proposed in WO 91/04024 and in EP-A-0446699.

It has recently become apparent that there are at least three types of NO synthase as follows:

(i) a constitutive, Ca⁺⁺/calmodulin dependent enzyme, located in the endothelium, that releases NO in response to receptor or physical stimulation.

(ii) a constitutive, Ca⁺⁺/calmodulin dependent enzyme, located in the brain, that releases NO in response to receptor or physical stimulation.

(iii) a Ca⁺⁺ independent enzyme which is induced after activation of vascular smooth muscle, macrophages, endothelial cells, and a number of other cells by endotoxin and cytokines. Once expressed this inducible NO synthase synthesizes NO for long periods.

The NO released by the constitutive enzymes acts as a transduction mechanism underlying several physiological responses. The NO produced by the inducible enzyme is a cytotoxic molecule for tumor cells and invading microorganisms. It also appears that the adverse effects of excess NO production, in particular pathological vasodilation and tissue damage, may result largely from the effects of NO synthesized by the inducible NO synthase.

There is also a growing body of evidence that NO may be involved in the degeneration of cartilage which takes place in certain conditions such as arthritis and it is also known that NO synthesis is increased in rheumatoid arthritis. Accordingly, further conditions in which there is an advantage in inhibiting NO production from L-arginine include autoimmune and/or inflammatory conditions affecting the joints, for example arthritis, inflammatory bowel disease, cardiovascular ischemia, diabetes, hyperalgesia (allodynia), cerebral ischemia (both focal ischemia, thrombotic stroke and global ischemia, secondary to cardiac arrest), and other CNS disorders mediated by NO.

Further conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy.

Some of the NO synthase inhibitors proposed for therapeutic use so far, and in particular L-NMMA, are non-selective in that they inhibit both the constitutive and the inducible NO synthase. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use.

WO94/12165, WO94/14780, WO93/13055, EP0446699A1, U.S. Pat. No. 5,132,453 and PCT/US95/02669 disclose compounds that inhibit nitric oxide synthesis and preferentially inhibit the inducible isoform of nitric oxide synthase. The disclosures of the U.S. Patent is hereby incorporated by reference in its entirety as if written herein.

SUMMARY OF THE INVENTION

In accordance with the present invention novel amino alcohol amine derivatives of L-N⁶-(1-iminoethyl)lysine derivatives are provided. These novel inhibitor compounds can be represented by the following chemical formula. A compound or a pharmaceutically acceptable salt, prodrug or ester therof having the formula (I):

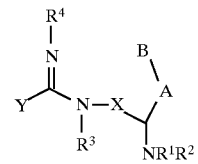

Y is a hydrogen, lower alkyl radical, lower alkenyl radical, lower alkynyl radical, aromatic hydrocarbon radical, alicyclic hydrocarbon radical, amino, heterocyclyl radical in which 1 to about 4 heteroatoms are independently selected from oxygen, nitrogen and sulfur, wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkyl radical, lower alkenyl radical, lower alkynyl radical, aromatic hydrocarbon radical, $(CH_2)_mQ(CH_2)_n$, where m=1–3, n=1–3, and Q is sulfur, sulfinyl, sulfonyl or oxygen, C=O, lower alkynyl radical, aromatic hydrocarbon radical, alicyclic hydrocarbon radical or heterocyclyl radicals in which 1 to about 4 heteroatoms are independently selected from oxygen, nitrogen and sulfur, wherein all said radicals are optionally substituted with hydrogen, halogen and lower alkyl;

$R^1$, $R^2$, $R^3$ and $R^4$ are independently selected from the group consisting of hydrogen and lower alkyl;

A is a lower alkyl radical wherein said radical is optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals; or A can be a direct bond to the remainder of the molecule B is $CH_2R^5$ where $R^5$ is amidine, guandine, sulfonamide, amino which may be optionally substituted with alkyl, alkylaryl or aryl radicals.

In another broad aspect, the present invention is directed to inhibiting nitric oxide synthesis in a subject in need of such inhibition or treatment by administering a compound of Formula (I) which preferentially inhibits the inducible isoform of nitric oxide synthase over the constitutive isoform of nitric oxide synthase, in a nitric oxide synthesis inhibiting amount to such subject.

The invention further relates to a pharmaceutical composition comprising a compound from Formula (I).

Compounds and compositions defined above have usefulness as inhibitors of nitric oxide synthase. These compounds also preferentially inhibit the inducible form over the constitutive form by at least 3 fold.

Conditions in which there is an advantage in inhibiting NO production from L-arginine include systemic hypotension associated with septic and/or toxic shock induced by a wide variety of agents; therapy with cytokines such as TNF, IL-1 and IL-2; and as an adjuvant to short term immunosuppression in transplant therapy. Further conditions in which there is an advantage in inhibiting NO production from L-arginine include autoimmune diseases and/or inflammatory conditions such as those affecting the joints, for example arthritis or inflammatory bowel disease, cardiovascular ischemia, diabetes, cerebral ischemia and other CNS disorders mediated by NO.

A preferred embodiment of the present invention is a compound of the formula (I) wherein Y is hydrogen or lower alkylene X is lower alkylene from 3–5 carbon A is lower alkylene from 1–3 carbons optionally substituted with hydroxyl or a direct bond connected to the remainder of the molecule.

It is preferred that Y is methyl, X is preferably butylene, $R^1$, $R^2$, $R^3$, and $R^4$ are preferably hydrogen, and A is preferably lower alkyl or a direct bond to the remainder of the molecule.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable salts may be of utility in the preparation and purification of the compound in question. Thus, preferred salts include those formed from hydrochloric, hydrobromic, sulfuric, citric, tartaric, phosphoric, lactic, acetic, succinic, fumaric, maleic, methanesulfonic, ethanesulfonic, p-toluenesulfonic, benzenesulfonic and the like. (See, for example, S. M. Berge et al., Pharmaceutical Salts, *J. Pharm. Sci.*, 1977, 66, 1–19.) Salts of the compounds of formula (I) can be made by reacting the appropriate compound in the form of the free base with the appropriate acid.

While it may be possible for the compounds of formula (I) to be administered as the raw chemical, it is preferable to present them as a pharmaceutical formulation. According to a further aspect, the present invention provides a pharmaceutical formulation comprising a compound of formula (I) or a pharmaceutically acceptable salt or solvate thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of formula (I) or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As utilized herein, the term "lower alkyl", alone or in combination, means an acyclic alkyl radical containing from 1 to about 10, preferably from 1 to about 8 carbon atoms and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "lower alkenyl" refers to an unsaturated acyclic hydrocarbon radical in so much as it contains at least one double bond. Such radicals containing from about 2 to about 10 carbon atoms, preferably from about 2 to about 8 carbon atoms and more preferably 2 to about 6 carbon atoms. Examples of suitable alkenyl radicals include propylenyl, buten-1-yl, isobutenyl, pentenylen-1-yl, 2-2-methylbuten-1-yl, 3-methylbuten-1-yl, hexen-1-yl, hepten-1-yl, and octen-1-yl, and the like.

The term "lower alkynyl" refers to an unsaturated acyclic hydrocarbon radical in so much as it contains one or more triple bonds, such radicals containing about 2 to about 10 carbon atoms, preferably having from about 2 to about 8 carbon atoms and more preferably having 2 to about 6 carbon atoms. Examples of suitable alkynyl radicals include ethynyl, propynyl, butyn-1-yl, butyn-2-yl, pentyn-1-yl, pentyn-2-yl, 3-methylbutyn-1-yl, hexyn-1-yl, hexyn-2-yl, hexyn-3-yl, 3,3-dimethylbutyn-1-yl radicals and the like.

The term "alicyclic hydrocarbon" or "cycloalkyl" means a aliphatic radical in a ring with 3 to about 10 carbon atoms, and preferably from 3 to about 6 carbon atoms. Examples of suitable alicyclic radicals include cyclopropyl, cyclobutyl, cyclopentyl, cyclohexyl, cyclohexenyl and the like.

The term "aromatic hydrocarbon radical" means 4 to about 16 carbon atoms, preferably 6 to about 12 carbon atoms, more preferably 6 to about 10 carbon atoms. Examples of suitable aromatic hydrocarbon radicals include phenyl, naphthyl, and the like.

The term "aryl" as used herein means 5- and 6-membered single-aromatic radicals which may include from zero to four heteroatoms. Representative aryls include phenyl, thienyl, furanyl, pyridinyl, (is)oxazoyl and the like.

The term DCM means dichloromethane.

The term DEAD means diethyl azodicarboxylate.

The term DIBAL-H means diisobutylaluminum hydride.

The term DMAP means dimethylaminopyridine.

The term DMSO means dimethylsulfoxide.

The term EDC means 1-(3-dimethylaminopropyl)-3-ethylcarbodiimide hydrochloride.

The term "heterocyclyl radical" means a saturated or unsaturated cyclic hydrocarbon radical including aromatic systems with 4 to about 10 carbon atoms, preferably about 5 to about 6; wherein 1 to about 4 carbon atoms are replaced by nitrogen, oxygen or sulfur. The "heterocyclic radical" may be fused to an aromatic hydrocarbon radical. Suitable examples include pyrrolyl, pyridinyl, pyrazolyl, triazolyl, pyrimidinyl, pyridazinyl, oxazolyl, isoxazolyl, thiazolyl, imidazolyl, indolyl, thienyl, furanyl, tetrazolyl, 2-pyrrolinyl, 3-pyrrolinyl, pyrrolindinyl, 1,3-dioxolanyl, 2-imidazonlinyl, imidazolidinyl, 2-pyrazolinyl, pyrazolidinyl, isoxazolyl, isothiazolyl, oxadiazolyl, triazolyl, thiadiazolyl, 2H-pyranyl, 4H-pyranyl, piperidinyl, 1,4-dioxanyl, morpholinyl, 1,4-dithianyl, thiomorpholinyl, pyrazinyl, piperazinyl, triazinyl, 1,3,5-trithianyl, benzo(b)thiophenyl, benzimidazolyl, quinolinyl, and the like.

The term HOBT means N-hydroxybenzotriazole.

The term "lower alkoxy", alone or in combination, means an alkyl ether radical wherein the term alkyl is as defined above and most preferably containing 1 to about 4 carbon atoms. Examples of suitable alkyl ether radicals include methoxy, ethoxy, n-propoxy, isopropoxy, n-butoxy, iso-butoxy, sec-butoxy, tert-butoxy and the like.

The term "lower thioalkoxy", alone or in combination, means an alkyl thioether radical wherein the term alkyl is as defined above and most preferably containing 1 to about 4 carbon atoms. Examples of suitable alkyl thioether radicals include thiomethoxy, thioethoxy, thio-n-propoxy, thio-i-propoxy, thio-n-butoxy, thio-iso-butoxy, thio-sec-butoxy, thio-tert-butoxy and the like.

The term alkoxycarbonyl as used herein means an alkoxy group, as defined above, having a carbonyl (C=O) group attached.

The term "halogen" means fluorine, chlorine, bromine or iodine.

The term mcpba means m-chloroperbenzoic acid.

The term NMM means N-methylmorpholine.

The term NMMO means 4-methylmorpholine N-oxide.

The term "prodrug" refers to a compound that is made more active in vivo.

The term sulfinyl means SO.

The term sulfonyl means $SO_2$.

The term TEA means triethylamine.

The term $TMSN_3$ means azidotrimethylsilane.

As used herein, reference to "treatment" of a patient is intended to include prophylaxis.

All references, patents or applications, U.S. or foreign, cited in the application are hereby incorporated by reference as if written herein.

Compounds of the present invention can exist in geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention.

Disclosed are four general synthetic processes useful in the preparation of the compounds of the present invention.

Scheme 1

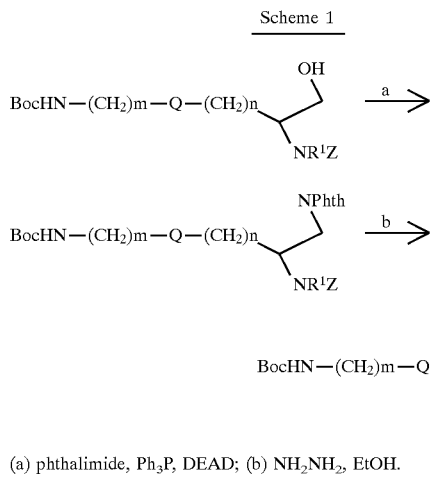

(a) phthalimide, Ph₃P, DEAD; (b) NH₂NH₂, EtOH.

Scheme 2

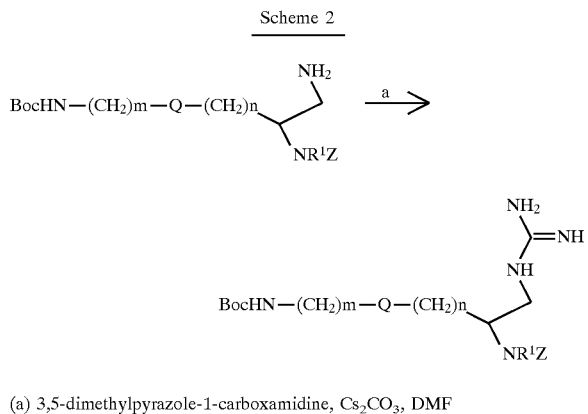

(a) 3,5-dimethylpyrazole-1-carboxamidine, Cs₂CO₃, DMF

Scheme 3

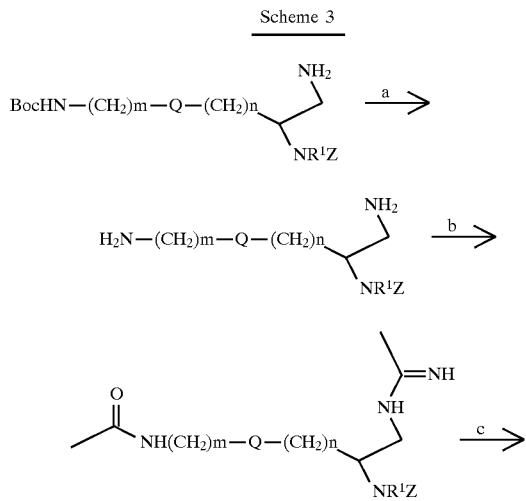

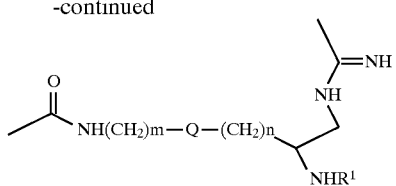

(a) HCl/dioxane, HOAc; (b) methyl acetimidate, DMF, TEA; (c) H₂, Pd, EtOH.

Scheme 4

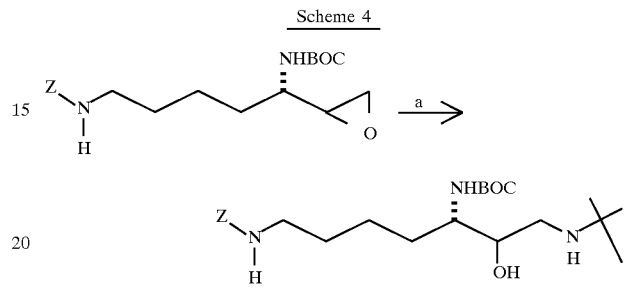

(a) t-butylamine, DCM.

Without further elaboration, it is believed that one skilled in the art can, using the preceding description, utilize the present invention to its fullest extent. Therefore the following preferred specific embodiments are to be construed as merely illustrative and not limitative of the remainder of the disclosure in any way whatsoever.

All experiments were performed under either dry nitrogen or argon. All solvents and reagents were used without further purification unless otherwise noted. The routine work-up of the reactions involved the addition of the reaction mixture to a mixture of either neutral, or acidic, or basic aqueous solutions and organic solvent. The aqueous layer was extracted n times (x) with the indicated organic solvent. The combined organic extracts were washed n times (x) with the indicated aqueous solutions, dried over anhydrous $Na_2SO_4$, filtered, concentrated in vacuo, and purified as indicated. Separations by column chromatography were achieved with conditions described by Still. (Still, W. C.; Kahn, M.; Mitra, A. Rapid Chromatograhic Technique for Preparative Separation with Moderate Resolution. *J. Org. Chem.*, 1978, 43, 2923–2925.) The hydrochloride salts were made from 1N HCl, HCl in ethanol (EtOH), 2N in MeOH, or 6N HCl in dioxane. Thin layer chromatograms were run on 0.25 mm EM precoated plates of silica gel 60 F254. High performance liquid chromatograms (HPLC) were obtained from C-8 or C-18 reverse phase columns which were obtained from several vendors. Analytical samples were dried in an Abderhalden apparatus at either 56° C. or 78° C. $^1$H NMR spectra were obtained from either General Electric QE-300 or Varian VXR 400 MHz spectrometer with tetramethylsilane as an internal standard. $^{13}$C NMR were obtained from a Varian spectrometer at 125.8 MHz with tetramethylsilane as an internal standard.

EXAMPLE 1

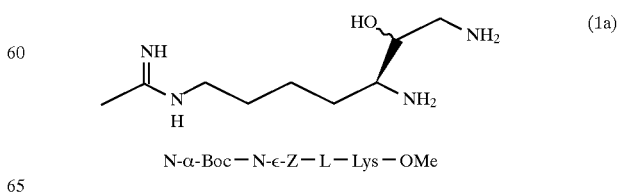

N-α-Boc—N-ε-Z—L—Lys—OMe

1a. To a stirring solution of cesium carbonate (32.6 g, 0.10 mol) in 150 mL DMF was added N-α-Boc-N-ε-Z-Lys (68.3 g, 0.18 mol). After 10 min, iodomethane (51.1 g, 0.36 mol) was added. After 18 h, solvent was removed in vacuo. The resultant gum was washed with hexane and the hexane was decanted. The product was dissolved in 100 mL of DCM and filtered through a 100×70 mm pad of EM silica gel. The silica was washed with 900 mL DCM and 300 mL EtOAc which were combined. The solvent was removed in vacuo to yield 66.4 g (94%) of product.

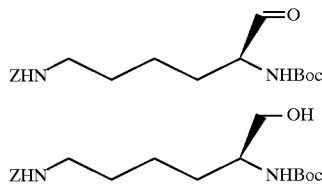

1b, c. To a stirring solution of 1a (7.9 g, 20 mmol) in 100 mL dry toluene cooled to −70° C. was added dropwise over 10 min 1M DIBAL-H in toluene (40 mL, 40 mmol). After stirring an additional 20 min, the reaction was quenched with 4 mL MeOH. Upon removal of the ice bath, 150 mL of saturated solution of Rochelle salt was added to the reaction. After stirring for 1 h, the layers were separated. The aqueous layer was extracted with 2×150 mL EtOAc. The combined organic layers were washed with 2×200 mL $H_2O$, dried, filtered, and concentrated in vacuo. The residue was purified by flash chromatography according to Still et al. to yield 5.37 g (74%) of 1b and 0.70 g (10%) of 1c. Both 1b and 1c were white solids.

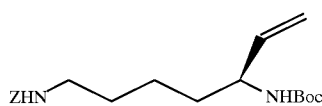

1d. To a stirring suspension of methyltriphenylphosphonium bromide (2.18 g, 6.1 mmol) in 50 mL of $Et_2O$ was added dropwise 0.5M potassium hexamethyldisilazide in toluene (12.2 mL, 6.1 mmol). After stirring for 1.5 h, 1b (2.22 g, 6.1 mmol) in 50 mL of $Et_2O$ was added. After 16 h, a white solid was filtered from the reaction. The filtrate was concentrated in vacuo. The residue was purified by flash chromatography to yield 1.11 g (50%) of 1d, a clear colorless gum. Anal calcd for $C_{20}H_{30}N_2O_4 \cdot 0.2\ H_2O$: C, 65.62; H, 8.37; N, 7.65. Found: C, 65.65; H, 8.07; N, 7.59.

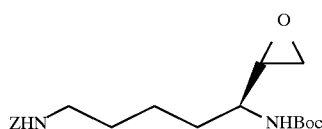

1e. To a stirring solution of 1d (3.62 g, 10 mmol) in 25 mL of DCM was added m-chloroperbenzoic acid (2.59 g, 15 mmol). After 16 h, solvent was removed under vacuum. The resulting residue was taken up in 100 mL of EtOAc and washed with 3×100 mL satd $KHCO_3$ solution. The organic layer was dried, filtered, and stripped. The crude product was purified by flash column chromatography to give 2.89 g (76%) of 1e.

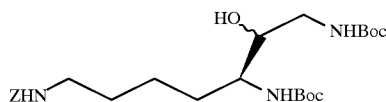

1f. To a stirring solution of t-butyl carbamate in THF −78° C. is added n-BuLi. After 30 min, 1e in THF is added to the reaction. After stirring for 16 h with warming to ambient temperature, the reaction is worked up in the usual manner.

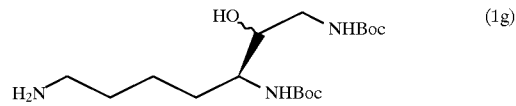

1g. Benzyloxycarbonyl protecting group is removed from 1f by catalytic hydrogenation using Pd black as the catalyst yielding 1g quantitatively.

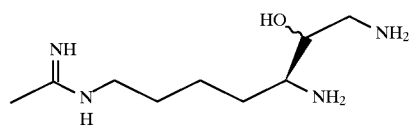

1. To a stirring solution of 1 g and TEA in DMF is added methyl acetimidate. After 16 h, TEA.HCl is filtered from the reaction and washed with a minimum of DMF. The filtrate is adjusted to pH 3 with 1N HCl. The filtrate is concentrated under high vacuum. The residue is applied to a reverse phase column.

The purified product is treated with 1N HCl for 1 h at ambient temperature to give 1.

EXAMPLE 2

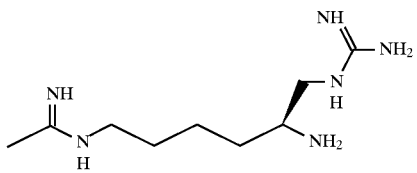

2. N-[5S-amino-6-[(aminoiminomethyl)amino]hexyl] ethanimidamide, trihydrochloride 2a. To a stirring solution of 1c (10.0 g, 27.2 mmol), triphenylphosphine (7.14 g, 27.2 mmol), and phthalimide (4.02 g, 27.2 mmol) in 30 mL of THF was added dropwise diethyl azodicarboxylate (4.28 mL, 27.2 mmol). After stirring over night at ambient temperature, the reaction was concentrated in vacuo and subsequently purified by column chromatography to yield 6.79 g (50%) of 2a.

2b To a stirring solution of 2a (4.06 g, 8.2 mmol) in 50 mL of EtOH-DCM (1:1) was added hydrazine (1.28 mL, 41 mmol). After stirring over weekend at ambient temperature, reaction was triturated with hot DCM and filtered. This was repeated. The filtrate was concentrated in vacuo. The product was a clear colorless glass. The yield of 2b was 2.34 g (81%).

2c To a stirring solution of 2b (1.76 g, 5.0 mmol) and cesium carbonate (0.90 g, 2.75 mmol) in 10 mL DMF was added 3,5-dimethylpyrazole-1-carboxamidine nitrate. After 20 h, the reaction was filtered. To the filtrate was added HOAc. After concentrating filtrate under vacuum, the residue was triturated with $Et_2O$ to give 1.11 g (54%) of product.

2d. Benzyloxycarbonyl protecting group was removed from 2c by catalytic hydrogenation using Pd black as the catalyst yielding 2d quantitatively.

11

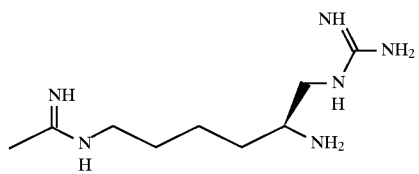

2 Example 2 was prepared in the same manner as described in Example 1 starting with 2d (0.90 g, 2.4 mmol) to give 0.44 g (47%). Anal. Calcd for $C_9H_{22}N_6 \cdot 3$ HCl$\cdot$2.5 H$_2$O: C, 29.32; H, 8.20; N, 22.79; Cl, 28.84. Found: C, 29.67; H, 8.36; N, 22.07; Cl, 27.10.

EXAMPLE 3

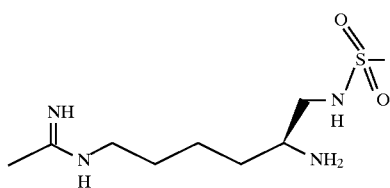

3. N-[5S-amino-6-[(methylsulfonyl)amino]hexyl] ethanimidamide, dihydrochloride

3a. To a stirring solution of 2b (1.76 g, 5.0 mmol), TEA (0.83 mL, 6.0 mmol) and DMAP (0.06 g, 0.05 mmol) in 25 mL of DCM and 2 mL of DMF cooled to 5° C. was added methanesulfonyl chloride (0.46 mL, 6.0 mmol). After stirring 72 h with warming to ambient temperature, the solvent was removed under vacuum. The residue was partitioned between 100 mL of EtOAc and 100 mL 1M KHSO$_4$. After separating the layers, the organic layer was washed with 2×100 mL 1M KHSO$_4$, 2×100 mL H$_2$O. The organic phase was worked up in the usual manner to obtain 1.66 g (75%) of a white crystalline product.

3b. Benzyloxycarbonyl protecting group was removed from 3a (1.33 g, 3.0 mmol) by catalytic hydrogenation using Pd black as the catalyst yielding 3b quantitatively.

3c. To a stirring solution of 3b (1.11 g, 3.0 mmol) and TEA (4.2 mL, 30 mmol, 3.0 mmol) in 5 mL of DMF was added methyl acetimidate (1.64 g, 15.0 mmol). After 16 h, TEA.HCl was filtered from the reaction and washed with a minimum of DMF. The filtrate was adjusted to pH 3 with 1N HCl. The filtrate was concentrated under high vacuum. The residue was applied to a reverse phase column. The yield of 3c was 0.66 g (57%).

3 To a stirring solution of 3c (0.65 g, 1.7 mmol) in 10 mL of HOAc was added 10 mL of 4N HCl/dioxane. After 15 min, the solvent was removed under vacuum. The product was lyophilized from H$_2$O to give 0.53 g (98%) of 3. Anal. Calcd for $C_9H_{22}N_4O_2S \cdot 2$ HCl$\cdot$0.7 H$_2$O$\cdot$0.8 HOAc: C, 32.90; H, 7.54; N, 14.75; Cl, 18.67. Found: C, 33.23; H, 7.38; N, 14.51; Cl, 18.30.

EXAMPLE 4

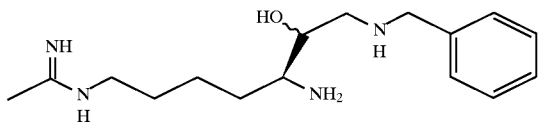

4 Example 4 is prepared in same manner as described in Example 1 starting with 1e and benzylamine.

12

EXAMPLE 5

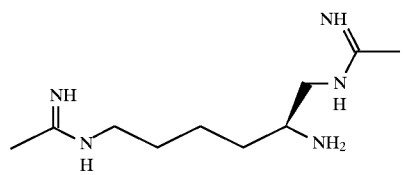

5a. Example 5a is prepared from 2b. Benzyloxycarbonyl protecting group is removed from 2b by catalytic hydrogenation using Pd black as the catalyst yielding 5a quantitatively.

5. Example 5 is prepared in the same manner as Example 1 starting with 5a.

EXAMPLE 6

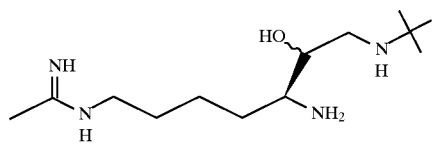

6. Example 6 is prepared in same manner as described in Example 1 starting with 1e and t-butylamine.

EXAMPLE 7

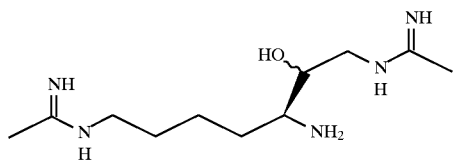

7a. Example 7a is prepared from 1e and benzyl carbamate as described in 1f.

7b. Benzyloxycarbonyl protecting group are removed from 7a by catalytic hydrogenation using Pd black as the catalyst.

7. Example 7 is prepared in the same manner as described in Example 1 starting with 7b.

Biological Data

The activity of the above listed compounds as NO synthase inhibitors has been determined in the following assays:

Citrulline Assay for Nitric Oxide Synthase

Nitric oxide synthase activity was measured by monitoring the conversion of L-[2,3-3H]-arginine to L-[2,3-3H]-citrulline (1,2). The cDNA for human inducible NOS (hiNOS) was isolated from a λcDNA library made from RNA extracted from a colon sample from a patient with ulcerative colitis; human endothelial constitutive NOS (hecNOS) was isolated from a λcDNA library made from RNA extracted from human umbilical vein endothelial cells (HUVEC); and human neuronal constitutive NOS (hncNOS) was isolated from a λcDNA library made from RNA extracted from human cerebellum from a cadaver. The recombinant enzymes were expressed in insect cells using a baculovirus vector. Enzyme activity was isolated from cell extracts and partially purified by DEAE-Sepharose chromatography (2). Enzyme and inhibitors were added to give a volume of 50 μL in 50 mM Tris (pH 7.6) and the reaction initiated by the addition of 50 μL of a solution containing 50 mM Tris (pH 7.6), 2.0 mg/mL bovine serum albumin, 2.0 mM DTT, 4.0 mM CaCl2, 20 μM FAD, 100 μM tetrahydrobiopterin, 0.4–2.0 mM NADPH and 60 μM L-arginine containing 0.9 μCi of L-[2,3-3H]-arginine. For constitutive NOS, calmodulin was included at a final concentration of 40–100 nM. Following incubation at 37° C. for 15 minutes, the reaction was terminated by addition of 300 μL cold buffer containing 10 mM EGTA, 100 mM HEPES (pH5.5) and 1.0 mM L-citrulline. The [3H]-citrulline was separated by chromatography on Dowex 50W X-8 cation exchange resin and radioactivity quantified with a liquid scintillation counter.

1. Bredt, D. S. and Snyder, S. H. (1990) Proc. Natl. Acad. Sci. U.S.A. 87, 682–685.
2. Misko, T. P., Moore, W. M., Kasten, T. P., Nickols, G. A., Corbett, J. A., Tilton, R. G., McDaniel, M. L., Williamson, J. R. and Currie, M. G. (1993) Eur. J. Pharm. 233, 119–125.

The following examples were assayed with the following results.

| Example number | hiNOS IC$_{50}$ (μM) | hecNOS IC$_{50}$ (μM) | hncNOS IC$_{50}$ (μM) |
|---|---|---|---|
| 2 | 22 | 479 | 35 |
| 3 | 106 | 6620 | 837 |

From the foregoing description, one skilled in the art can easily ascertain the essential characteristics of this invention, and without departing from the spirit and scope thereof, can make various changes and modifications of the invention to adapt it to various usages and conditions.

What is claimed:

1. A compound or a pharmaceutically acceptable salt thereof having the formula:

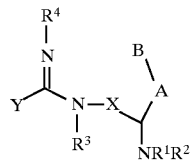

Y is a hydrogen; lower alkyl radical; lower alkenyl radical; lower alkynyl radical; aromatic hydrocarbon radical; alicyclic hydrocarbon radical; heterocyclyl radical in which 1 to about 4 heteroatoms are independently selected from oxygen, nitrogen and sulfur; wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical; lower alknylene radical; lower alkynylene radical; aromatic hydrocarbon radical, $(CH_2)_mQ(CH_2)_n$, where m=1–3, n=1–3, and Q is sulfur, sulfinyl, sulfonyl, oxygen, C=O, lower alkynyl radical, aromatic hydrocarbon radical, alicyclic hydrocarbon radical or heterocyclyl radicals in which 1 to about 4 heteroatoms are independently selected from oxygen, nitrogen and sulfur; wherein all said radicals are optionally substituted with hydrogen, halogen and lower alkyl;

$R^1$, $R^2$, $R^3$ and $R^4$ are independently selected from the group consisting of hydrogen and lower alkyl;

A is a lower alkylene radical wherein said radical is optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals; or A can be a direct bond to the remainder of the molecule; and B is $CH_2R^5$ where $R^5$ is amidino, guanidino, sulfonamidino, amino which may be optionally substituted with alkyl, aklyaryl or aryl radicals.

2. The compound as recited in claim 1 wherein:
Y is hydrogen or lower alkyl;
X is lower alkylene from 3–5 carbons; and
A is lower alkylene from 1–3 carbons optionally substituted with hydroxyl or a direct bond to the remainder of the molecule.

3. The compound as recited in claim 1 wherein:
Y is methyl;
X is butylene;
$R^1$, $R^2$, $R^3$, and $R^4$ are hydrogen; and
A is lower alkylene from 1–3 carbons optionally substituted with hydroxyl.

4. The compound as recited in claim 1 wherein the compound is selected from the group consisting of:
N-[5S-amino-6[(aminoiminomethyl)amino]hexyl]-ethanimidamide, trihydrochloride; and N-[5S-amino-6-[(methylsulfonyl)amino]hexyl]-ethanimidamide, dihydrochloride.

5. A pharmaceutical composition comprising a compound or a pharmaceutically acceptable salt thereof having the formula:

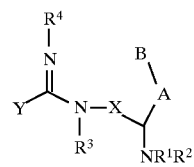

Y is a hydrogen; lower alkyl radical; lower alkenyl radical; lower alkynyl radical; aromatic hydrocarbon radical; alicyclic hydrocarbon radical; heterocyclyl radical in which 1 to about 4 heteroatoms are independently selected from oxygen, nitrogen and sulfur; wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical; lower alkenylene radical; lower alkynylene radical; aromatic hydrocarbon radical; $(CH_2)_mQ(CH_2)_n$, where m=1–3, n=1–3, and Q is sulfur, sulfinyl, sulfonyl, oxygen, C=O, lower alkynylene radical, aromatic hydrocarbon radical, alicyclic hydrocarbon radical or heterocyclyl radicals in which 1 to about 4 heteroatoms are independently selected from oxygen, nitrogen and sulfur; wherein all said radicals are optionally substituted with hydrogen, halogen and lower alkyl;

$R^1$, $R^2$, $R^3$ and $R^4$ are independently selected from the group consisting of hydrogen and lower alkyl;

A is a lower alkylene radical wherein said radical is optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals; or A can be a direct bond to the remainder of the molecule; and B is CH$_2$R$^5$ where R$^5$ is amidino, guanidino, sulfonamido, amino which may be optionally substituted with alkyl, aklyaryl or aryl radicals;

together with a pharmaceutically acceptable carrier.

6. The pharmaceutical composition of claim 5 wherein:

Y is hydrogen or lower alkyl;

X is lower alkylene from 3–5 carbons; and

A is lower alkylene from 1–3 carbons optionally substituted with hydroxyl or a direct bond to the remainder of the molecule.

7. The pharmaceutical composition of claim 6 wherein:

Y is methyl;

X is butylene;

R$^1$, R$^2$, R$^3$, and R$^4$ are hydrogen; and

A is lower alkylene from 1–3 carbons optionally substituted with hydroxyl.

8. The pharmaceutical composition of claim 5 wherein the compound is selected from the group consisting of:

N-[5S-amino-6[(aminoiminomethyl)amino]hexyl]-ethanimidamide, trihydrochloride; and N-[5S-amino-6-[(methylsulfonyl)amino]hexyl]-ethanimidamide, dihydrochloride.

9. A method of inhibiting nitric oxide synthesis in a subject in need of such inhibition by administering a therapeutically effective amount of a compound or a pharmaceutically acceptable salt thereof having the formula:

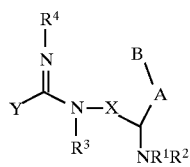

Y is a hydrogen; lower alkyl radical; lower alkenyl radical; lower alkynyl radical; aromatic hydrocarbon radical; alicyclic hydrocarbon radical; amino; heterocyclyl radical in which 1 to about 4 heteroatoms are independently selected from oxygen, nitrogen and sulfur; wherein all said radicals may optionally be substituted with hydrogen, cyano, lower alkyl, nitro, amino, alicyclic hydrocarbon radicals, or aromatic hydrocarbon radicals which may be optionally substituted with lower alkyl;

X is lower alkylene radical; lower alkenylene radical; lower alkynylene radical; aromatic hydrocarbon radical; (CH$_2$)$_m$Q(CH$_2$)$_n$, where m=1–3, n=1–3, and Q is sulfur, sulfinyl, sulfonyl, oxygen, C=O, lower alkynylene radical, aromatic hydrocarbon radical, alicyclic hydrocarbon radical or heterocyclyl radicals in which 1 to about 4 heteroatoms are independently selected from oxygen, nitrogen and sulfur; wherein all said radicals are optionally substituted with hydrogen, halogen and lower alkyl;

R$^1$, R$^2$, R$^3$ and R$^4$ are independently selected from the group consisting of hydrogen and lower alkyl;

A is a lower alkylene radical wherein said radical is optionally substituted with hydrogen, lower alkyl, hydroxyl, lower alkoxy, alkoxycarbonyl, alkylaryloxy, thiol, lower thioalkoxy, thioalkylaryloxy, thioaryloxy, sulfinylalkyl, sulfinylalkylaryl, sulfinylaryl, sulfonylalkyl, sulfonylalkylaryl, sulfonylaryl, halogen, aromatic hydrocarbon radicals, or alicyclic hydrocarbon radicals; or A can be a direct bond to the remainder of the molecule; and B is CH$_2$R$^5$ where R$^5$ is amidino, guanidino, sulfonamido, amino which may be optionally substituted with alkyl, aklyaryl or aryl radicals.

10. The method of claim 9 wherein:

Y is hydrogen or lower alkylene;

X is lower alkylene from 3–5 carbons; and

A is lower alkylene from 1–3 carbons optionally substituted with hydroxyl or a direct bond to the remainder of the molecule.

11. The method of claim 10 wherein:

Y is methyl;

X is butylene;

R$^1$, R$^2$, R$^3$, and $^4$ are hydrogen; and

A is lower alkylene from 1–3 carbons optionally substituted with hydroxyl.

12. The pharmaceutical composition of claim 9 wherein the compound is selected from the group consisting of:

N-[5S-amino-6[(aminoiminomethyl)amino]hexyl]-ethanimidamide, trihydrochloride; and N-[5S-amino-6-[(methylsulfonyl)amino]hexyl]-ethanimidamide, dihydrochloride.

* * * * *